United States Patent [19]

Zagata et al.

[11] 4,170,570

[45] Oct. 9, 1979

[54] PROCESS FOR PREPARING OXIDATION CATALYSTS

[75] Inventors: Robert J. Zagata, Seven Hills; Wilfrid G. Shaw, Lyndhurst; David R. Woodbury, Bedford Hts., all of Ohio

[73] Assignee: Standard Oil Company (Ohio), Ohio

[21] Appl. No.: 866,572

[22] Filed: Jan. 3, 1978

[51] Int. Cl.² .................. B01J 27/14; B01J 29/16; B01J 29/00; B01J 29/10
[52] U.S. Cl. ............................ 252/437; 252/456; 252/458; 252/459; 252/464; 252/465; 252/468; 252/469
[58] Field of Search ............... 252/437, 464, 456, 458, 252/459, 465, 468, 469, 470, 466 J

[56] References Cited

U.S. PATENT DOCUMENTS

| | | | |
|---|---|---|---|
| 3,341,471 | 9/1967 | Callahan et al. | 252/454 X |
| 3,746,656 | 7/1973 | Shiraishi et al. | 252/437 |
| 3,755,434 | 8/1973 | Levy | 252/465 X |
| 3,778,386 | 12/1973 | Tokeraka et al. | 252/437 X |
| 3,801,670 | 4/1974 | Shiraishi et al. | 252/437 X |
| 3,875,220 | 4/1975 | White et al. | 252/437 X |
| 3,992,419 | 11/1976 | Otaki et al. | 252/437 X |
| 4,070,397 | 1/1978 | White et al. | 252/437 X |
| 4,075,127 | 2/1978 | Kodowoki et al. | 252/470 |
| 4,075,244 | 2/1978 | Akiyama et al. | 252/437 X |
| 4,092,354 | 5/1978 | Shiraishi et al. | 252/468 X |

*Primary Examiner*—Delbert E. Gantz
*Assistant Examiner*—William G. Wright
*Attorney, Agent, or Firm*—David J. Untener; Herbert D. Knudsen; Larry W. Evans

[57] ABSTRACT

A process for preparing an attrition resistant molybdenum-containing oxidation catalyst comprising; heat-treating the active catalytic components in an oxidizing atmosphere at a temperature in excess of 175° C.; refluxing the heat-treated oxide catalyst in an aqueous slurry of the required amount of support material; ball milling the resulting catalyst mixture; and subjecting the ball milled catalyst to a second heat-treating step in an oxidizing atmosphere, at a temperature in excess of 200° C.

9 Claims, No Drawings

PROCESS FOR PREPARING OXIDATION CATALYSTS

THE INVENTION

The present invention relates to a process for preparing molybdenum-containing solid oxidation catalysts of improved mechanical strength, and more particularly to a process for preparing molybdenum-containing oxidation catalysts having improved attrition resistance that are active for the production of unsaturated carboxylic acids and anhydrides.

The catalysts embodied in the present invention are molybdenum oxide-containing oxidation catalysts that are known for the oxidation of $C_3$- and $C_4$-$\alpha$, $\beta$-unsaturated aldehydes to the corresponding unsaturated acids as well as the conversion of $C_4$-paraffins, mono-olefins or diolefins to maleic anhydride, as more fully disclosed in U.S. Pat. Nos. 3,892,794, 3,893,951, 3,928,240, 3,956,377, 3,956,378, 4,017,423, 4,042,533, 3,904,653, 3,907,834, 3,919,257 and 4,021,427.

More specifically, those catalysts are contemplated that are composed of molybdenum oxide in combination with other metal oxides such as for example, vanadium and or tungsten, and which may also contain additional metal oxides as more specifically defined by the following empirical formula:

$$E_g G_h J_i Mo_{12} O_x$$

wherein

E is Sn, Cu, Ge, Sb, Bi, Te, Mn, As, alkali metals, Fe, Mg, Zn, Ni or mixture thereof;

G is W, Cr or mixture thereof; and

J is V, P, Sb, Co or mixture thereof; and wherein g and h are numbers from zero to about 20;

i is a number from greater than zero to about 20; and x is the number of oxygens required to satisfy the valence requirements of the other elements present.

Catalysts of the foregoing types often are preferably activated by thermal treatment in an oxygenated gas such as air or oxygen at an elevated temperature. These types of catalysts often are soft and have poor mechanical strength. Even when an active or inert support material prepared from silica sol or silica gel is incorporated into the catalyst mass prior to thermal activation, the finished catalyst is found to be generally poor in physical properties, particularly in resistance to attrition, and/or to have a reduced catalytic response.

Surprisingly, it has been found that solid, physically durable oxidation catalysts comprising molybdenum oxide may be prepared by forming the oxides or oxide complexes of the active catalyst components, heat-treating the combined oxides in an oxidizing atmosphere at a temperature in excess of at least 175° C., refluxing the heat-treated oxide catalyst in an aqueous slurry of the required amount of the carrier material; ball milling the heat-treated catalyst; followed by drying and subjecting the dried material to a second and final heat-treating step in an oxidizing atmosphere at a temperature in excess of 200° C.

The catalyst support may be derived from sol-type or a solid form of the support material, or any combination of the sol and solid form. Although silica is the preferred carrier in this invention other supporting materials may be employed including alumina, titania, zirconia, metal phosphates such as boron phosphate, aluminum phosphate, zirconium phosphate and the like. In the process of this invention an aqueous silica suspension, dispersion, sol or gel is preferred. Silica sols as commercially prepared and/or derived from water glass, silicon halides, and silicates are all useful in the preparation of the attrition resistant catalysts embodied herein. The silica sols useful herein may contain as little as 5% by weight or less up to 60% by weight or more of silica, the main requirement being that there be sufficient water present for ball milling.

The catalysts prepared according to the process of the present invention exhibit a high degree of physical strength even at high concentration levels of the active components. Thus a wide concentration range of active components can be utilized without experiencing any loss of physical strength or selectivity, and concentrations of from about 30 to 90 percent by weight of the active components of the final supported catalyst can advantageously be employed.

Although the process of this invention is particularly applicable to the preparation of catalysts employed in a fluid-bed reactor, the process may also be used in preparing shaped catalysts for use in a fixed-bed reactor. The shaping of the latter may be accomplished in several ways which are known in the art, as for example by extrusion, while the catalyst is in the form of a paste or slurry just prior to the final drying and thermal treatment. A microspheroidal form is readily obtained by spray drying of the catalyst slurry.

The preferred method of preparing an attrition resistant catalyst exemplified by a mixed oxide of molybdenum, vanadium, tungsten, copper and tin is as follows:

(A) The oxides of molybdenum ($MoO_3$), vanadium ($V_2O_5$), and tin ($SnO_2$) and tungsten metal are refluxed together, followed by the addition of copper acetate with additional refluxing;

(B) the resulting slurry is dried as by spray-drying or double drum drying, heat-treated or calcined in an oxidizing atmosphere at a temperature in the range of 175° to 500° C.;

(C) the heat-treated catalyst from (B) is refluxed in a silica sol, the amount of silica employed being dependent upon the desired concentration of silica in the final catalyst composition;

(D) The catalyst slurry resulting from step (C) is ball milled; and (E) The catalyst is then dried by spray drying and heat-treated in the same manner as in step (B) within temperature range of 200° to 500° C.

While the above mode of catalyst preparation is the preferred mode, various modifications of this procedure are also considered to be part of this invention. For example, the order in which the process steps are carried out may be varied. In one specific example, the attrition-resistance of the catalyst is likewise improved when the heat-treated metal oxide catalyst is ball-milled before it is refluxed in an aqueous slurry of the support material. It is an essential feature of the invention, however, that the support material be added to the active catalyst components subsequent to the initial heat-treating of the active components. Other procedural variations similar to the above that result in improved attrition characteristics of the catalyst are contemplated to be within the scope of the present invention.

Time, temperature, and the nature of the atmosphere under which the catalyst is heat-treated is generally selected on the basis of the catalyst composition and the activity desired in the specific catalytic process for which use it is intended. In general, when the temperature is raised, the time of heating extended and steam is provided in the heat treatment atmosphere, the resulting catalyst will be less catalytically active and may possess a lower surface area.

Although the proportion of the active component to the silica carrier in the final catalyst composition is not critical, it is desirable that at least 25% by weight of the total attrition resistant catalyst be made up of active component. The active component can made up as much as 90% or more of the total catalyst although it is preferred to have at least 10% by weight of silica present and more preferably to have about 20% or more by weight of silica present.

SPECIFIC EMBODIMENT

The attrition resistance of the catalysts of this invention was determined in a number of tests to demonstrate the importance of each of the process steps to the present invention. Finally, catalyst activity was determined to demonstrate that catalysts prepared according to the process of the instant invention, in addition to their attrition resistance, maintain their activity for the production of acrylic acid from acrolein.

The process of this invention is further illustrated in the following examples wherein the amounts of the various ingredients are expressed as parts by weight unless otherwise indicated. The effect of the essential features of the present process, as specified in steps A through E, on the attrition characteristics of the catalyst is demonstrated by Examples 1 through 10 and summarized in Tables 1 to 5 below.

The attrition characteristics of the catalysts in Example 1–10 were measured by a method described in "Test Methods for Synthetic Fluid Cracking Catalyst," page 43, American Cyanamid Company, 6131-4M-1/57. The attrition numbers reported represent the percent weight loss of the catalyst due to attrition between the time interval of 5 and 20 hours of test time. Thus the smaller the attrition number, the more resistant the catalyst is to attrition.

EXAMPLE 1

Preparation of the Catalyst Composition—50% $Mo_{12}V_3W_{1.2}Cu_2Sn_{0.5}O_{50.1}$—50% $SiO_2$ (A) 5323 grams of $MoO_3$, 792 grams of $V_2O_5$, 640 grams of tungsten metal and 220 grams of $SnO_2$ were added to 10 liters of distilled water that had been heated to 70° C., and the mixture of oxides was refluxed, cooled to 80° C., and hot copper acetate solution consisting of 1163 grams of copper acetate and 4.6 liters of distilled water was added. The mixture was refluxed again and the catalyst dried. (B) The dried catalyst was heat-treated at 390° C. for two hours. (C) 1814 Grams of the heat-treated oxide catalyst from step (B) was added to 2 liters of distilled water and ball milled for 15 hours. (D) 0.75 liters of distilled water and 4536 grams of silica sol containing 41% $SiO_2$ was added to the ball-milled catalyst. (E) The catalyst was then spray dried and heat-treated at 390° C. for 2 hours.

EXAMPLE 2

The procedure for preparing the catalyst of Example 1 was repeated with the exception that 15% of the total silica support was added in step (A) and 85% was added in step (D).

EXAMPLE 3

The procedure for preparing the catalyst of Example 1 was repeated with the exception that 25% of the total silica support was added in step (A) and 75% was added in step (D).

EXAMPLE 4

The procedure for preparing the catalyst of Example 1 was repeated with the exception that 33% of the total silica support was added in step (A) and 67% was added in step (D).

The advantage of adding all of the catalyst support material to the catalyst in a single step subsequent to the initial heat treating step (B) as in Example 1, compared with adding part of the support material in step (A) and the remainder in step (D) as in Examples 2 to 4, is shown by the comparisons drawn in Table I below.

TABLE I

| Example No. | Wt. % of Total SiO$_2$ added in Step (A) | Step (D) | Attrition No. |
| --- | --- | --- | --- |
| 1 | 0 | 100 | 7.2 |
| 2 | 15 | 85 | 16.0 |
| 3 | 25 | 75 | 30.6 |
| 4 | 33 | 67 | 36.8 |

EXAMPLE 5

The catalyst in Example 5 was prepared in the same manner as in Example 1 with the exception that heat-treating step (B) was omitted.

The beneficial effect of the heat-treating step (B) on the attrition resistance of the catalyst is shown by comparison of Examples 1 and 5 in Table II.

TABLE II

| Example | Heat-Treating as in Step (B) | Attrition No. |
| --- | --- | --- |
| 1 | yes | 7.2 |
| 5 | no | 29.9 |

EXAMPLE 6

The catalyst preparation employed in Example 1 was repeated with the exception that the silica sol was added subsequent to step (B) instead of in step (D) and was refluxed for one hour prior to ball-milling.

The advantage of refluxing a mixture of the active catalyst components with the support material on the attrition characteristics is shown by comparing Example 1 with Example 6 in Table III.

TABLE III

| Example | Reflux | Attrition No. |
| --- | --- | --- |
| 1 | No | 7.2 |
| 6 | Yes | 2.0 |

EXAMPLE 7

The catalyst preparation of Example 1 was repeated with the exception that the ball milling step (C) was omitted. The beneficial effect of ball milling is shown by comparing Example 1 & 7 in Table IV.

TABLE IV

| Example | Ball Milling | Attrition No. |
| --- | --- | --- |
| 1 | yes | 7.2 |

TABLE IV-continued

| Example | Ball Milling | Attrition No. |
|---------|--------------|---------------|
| 7 | no | 23.4 |

EXAMPLE 8

Preparation of catalyst composition—50% $Mo_{12}V_3W_{1.2}Cu_2Sn_{0.5}O_{50.1}$—50% $SiO_2$ 1814 grams of the heat-treated active catalyst component from step (B) of Example 1, were added to 5335 grams of silica sol containing 34 wt.% $SiO_2$. The mixture was refluxed for one hour, then ball-milled for 17 hours. To this was added 2.2 liters of distilled water, and the resulting aqueous slurry was spray dried and heat-treated at 390° C.

EXAMPLE 9

Preparation of catalyst composition—60% $Mo_{12}V_3W_{1.2}Cu_2Sn_{0.5}O_{50.1}$—40% $SiO_2$ The preparation of Example 8 was repeated with the exception that a 60 wt.% of the active catalytic components were combined with 40 wt.% of the silica support.

EXAMPLE 10

Preparation of catalyst composition—70% $Mo_{12}V_3W_{1.2}Cu_2Sn_{0.5}O_{50.1}$—30% $SiO_2$ The preparation of Example 8 was repeated with the exception that 70 wt.% of the active catalyst components were combined with 30 wt.% of the silica support.

A summary of the physical strengths of the catalysts in Example 8 to 10 and their activity for the conversion of acrolein to acrylic acid is demonstrated in Table V. The oxidation reaction was carried out in a fluid-bed reactor having an I.D. of 4.1 cms, employing a molar ratio of air, nitrogen, acrolein and water of 6/4/1/2, respectively, a reaction pressure of 12 psig, and a weight hourly space velocity of 0.10.

TABLE V

| Ex. No. | Wt. % Active Components | Attrition No. | Rx. Temp. °C. | Mole % Per Pass Conv. to Acrylic Acid | Mole % Select. to Acrylic Acid |
|---------|------------------------|---------------|---------------|---------------------------------------|-------------------------------|
| 8 | 50 | 2.5 | 265 | 85.8 | 86.0 |
| 9 | 60 | 3.0 | 254 | 87.9 | 88.1 |
| 10 | 70 | 2.0 | 252 | 87.6 | 88.5 |

The data shown in the above table substantiate the advantage of being able to prepare catalysts having various levels of active components present without any significant loss of physical strength or catalytic performance.

We claim:

1. A process for preparing an attrition-resistant molybdenum-containing solid oxidation catalyst comprising:
    forming the oxides or oxide complexes of the active catalytic components; heat-treating said catalytic oxides or oxide complexes in an oxidizing atmosphere at a temperature of from 175° to 500° C.; refluxing said heat-treated catalytic oxides in an aqueous slurry of a carrier material; ball milling said heat-treated catalytic oxides; and subjecting the resulting ball-milled catalytic oxides-carrier composition to a second heat treatment at a temperature in the range of 200° to 500° C. in an oxidizing atmosphere.

2. The process in claim 1 wherein the refluxing of the heat-treated catalytic oxides in the aqueous slurry of the carrier material is carried out prior to the ball-milling step.

3. The process in claim 1 wherein the heat-treated catalytic oxides are ball milled before being added to an aqueous slurry of the carrier material.

4. The process in claim 1 wherein the active catalyst has a composition represented by the empirical formula:

$$E_g G_h J_i Mo_{12}O_x$$

wherein
E is Sn, Cu, Ge, Sb, Bi, Te, Mn, As, alkali metals, Fe, Mg, Zn, Ni or mixture thereof;
G is W, Cr or mixture thereof; and
J is V, P, Sb, Co or mixture thereof; and wherein
g and h are numbers from zero to about 20;
i is a number from greater than zero to about 20; and
x is the number of oxygens required to satisfy the valence requirements of the other elements present.

5. The process in claim 4 wherein the catalyst contains 25–90% by weight of the active catalytic components.

6. The process in claim 5 wherein the carrier is silica.

7. The process in claim 5 wherein the catalyst contains at least 20% by weight of the carrier material.

8. The process in claim 6 wherein the silica carrier is employed in the form of a sol.

9. The process in claim 8 wherein the silica sol contains from 5 to 60% by weight of silica.

* * * * *